(12) United States Patent
Michihata et al.

(10) Patent No.: US 12,295,553 B2
(45) Date of Patent: May 13, 2025

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventors: Taihei Michihata, Tokyo (JP); Aki Mizukami, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 22 days.

(21) Appl. No.: 17/636,365

(22) PCT Filed: Aug. 26, 2020

(86) PCT No.: PCT/JP2020/032250
§ 371 (c)(1),
(2) Date: Feb. 18, 2022

(87) PCT Pub. No.: WO2021/039869
PCT Pub. Date: Mar. 4, 2021

(65) Prior Publication Data
US 2022/0287551 A1    Sep. 15, 2022

(30) Foreign Application Priority Data

Aug. 28, 2019   (JP) .................................. 2019-156097

(51) Int. Cl.
*A61B 1/045*  (2006.01)
*A61B 1/06*   (2006.01)
*G16H 30/40*  (2018.01)

(52) U.S. Cl.
CPC ............ *A61B 1/045* (2013.01); *A61B 1/0638* (2013.01); *A61B 1/0655* (2022.02); *G16H 30/40* (2018.01)

(58) Field of Classification Search
CPC ...... A61B 1/045; A61B 1/0655; A61B 1/0638; G16H 30/40

See application file for complete search history.

(56) References Cited

U.S. PATENT DOCUMENTS 6,975,899 B2 *  12/2005  Faupel ................. A61B 5/0071
                                                    600/407
11,246,476 B2 *  2/2022  Melsky .................. A61B 18/20
(Continued)

FOREIGN PATENT DOCUMENTS

CN        107548292 A      1/2018
EP         3618685 B1      6/2021
(Continued)

OTHER PUBLICATIONS

International Search Report and Written Opinion dated Nov. 24, 2020, received for PCT Application PCT/JP2020/032250, Filed on Aug. 26, 2020, 9 pages including English Translation.

*Primary Examiner* — Sunghyoun Park
(74) *Attorney, Agent, or Firm* — XSENSUS LLP

(57) ABSTRACT

A memory controller 931, in a first observation mode, writes a first captured image into a first memory area of a memory 92, reads first to fourth divided images obtained by dividing the first captured image from first to fourth divided areas of the first memory area, respectively, and outputs the first to fourth divided images to image processing units 932 to 935, respectively, and in a second observation mode, writes the first and second captured images into second and third memory areas, respectively, each having the same memory capacity as that of each of the divided areas in the memory 92, respectively, reads the first and second captured images from the second and third memory areas, respectively, and outputs the first and second captured images to two image processing units 932 and 933, respectively.

18 Claims, 8 Drawing Sheets

(56) References Cited

U.S. PATENT DOCUMENTS

| | | | |
|---|---|---|---|
| 11,607,119 B2* | 3/2023 | Bouali | A61B 5/4255 |
| 2009/0021739 A1* | 1/2009 | Tsujita | G01J 3/51 |
| | | | 356/407 |
| 2010/0134833 A1* | 6/2010 | Kitahara | G06K 15/1817 |
| | | | 358/1.15 |
| 2010/0245616 A1 | 9/2010 | Yoshino | |
| 2011/0050889 A1* | 3/2011 | Kiuchi | G06T 1/20 |
| | | | 348/135 |
| 2012/0151190 A1* | 6/2012 | Usuba | G06F 9/4843 |
| | | | 712/220 |
| 2013/0338438 A1 | 12/2013 | Watanabe | |
| 2014/0276008 A1 | 9/2014 | Steinbach et al. | |
| 2015/0381909 A1* | 12/2015 | Butte | A61B 1/0669 |
| | | | 250/578.1 |
| 2019/0004038 A1* | 1/2019 | Lim | G01N 33/6845 |
| 2019/0137394 A1 | 5/2019 | Kaneko | |
| 2022/0008156 A1* | 1/2022 | Tomatsu | G02B 23/2469 |

FOREIGN PATENT DOCUMENTS

| | | |
|---|---|---|
| JP | 2002135772 A | 5/2002 |
| JP | 2010218091 A | 9/2010 |
| JP | 2012123688 A | 6/2012 |
| JP | 2015-96920 A | 5/2015 |
| JP | 2016518197 A | 6/2016 |
| JP | 2017124127 A | 7/2017 |
| JP | 2018-79249 A | 5/2018 |
| JP | 2018-114592 * | 6/2018 |
| JP | 2018187023 A | 11/2018 |
| WO | WO-2016032729 A1 | 3/2016 |
| WO | WO-2018203473 A1 | 11/2018 |
| WO | 2019/087557 A1 | 5/2019 |

* cited by examiner

FIG.8
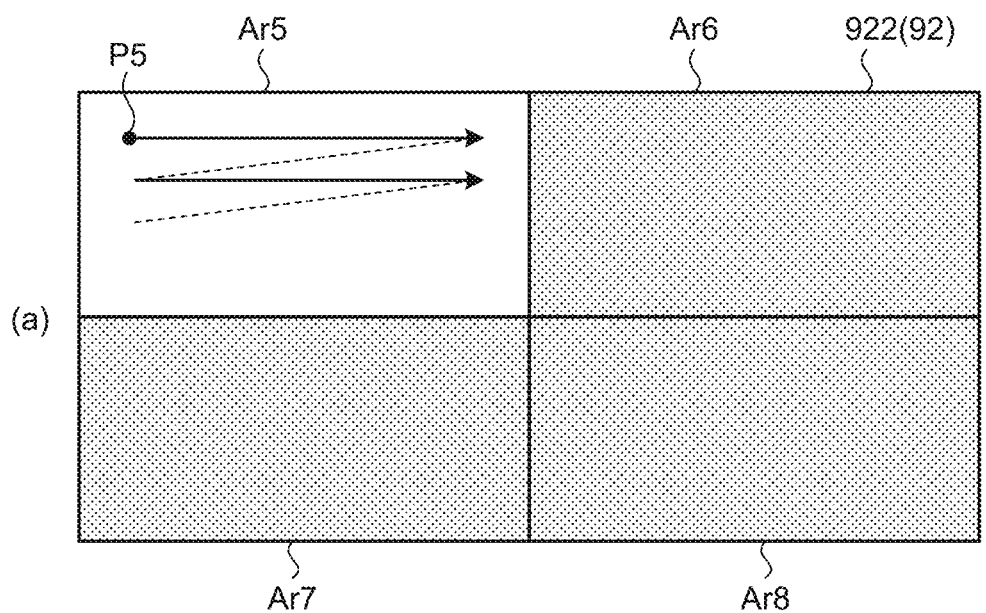
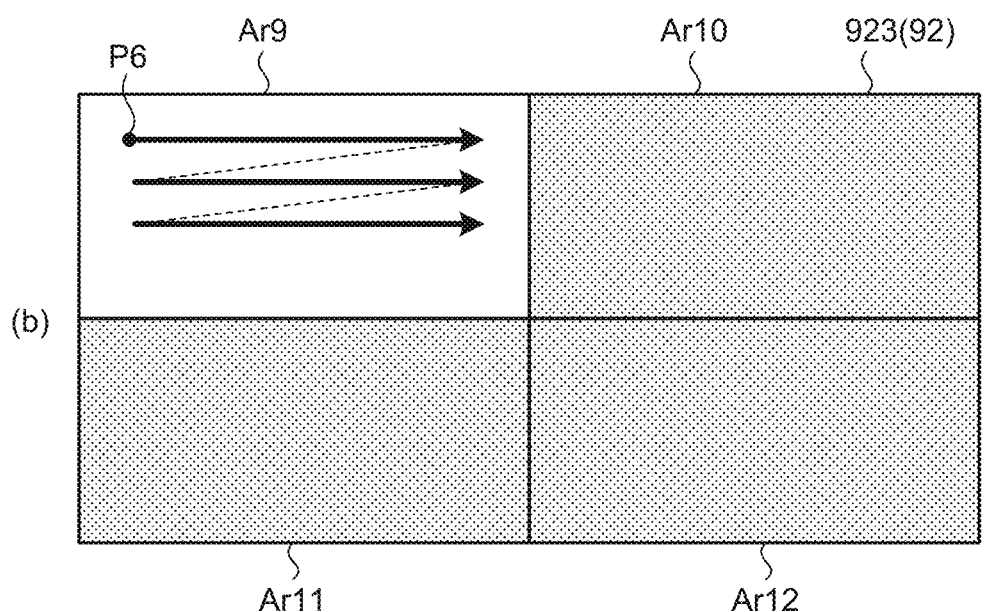

FIG.9
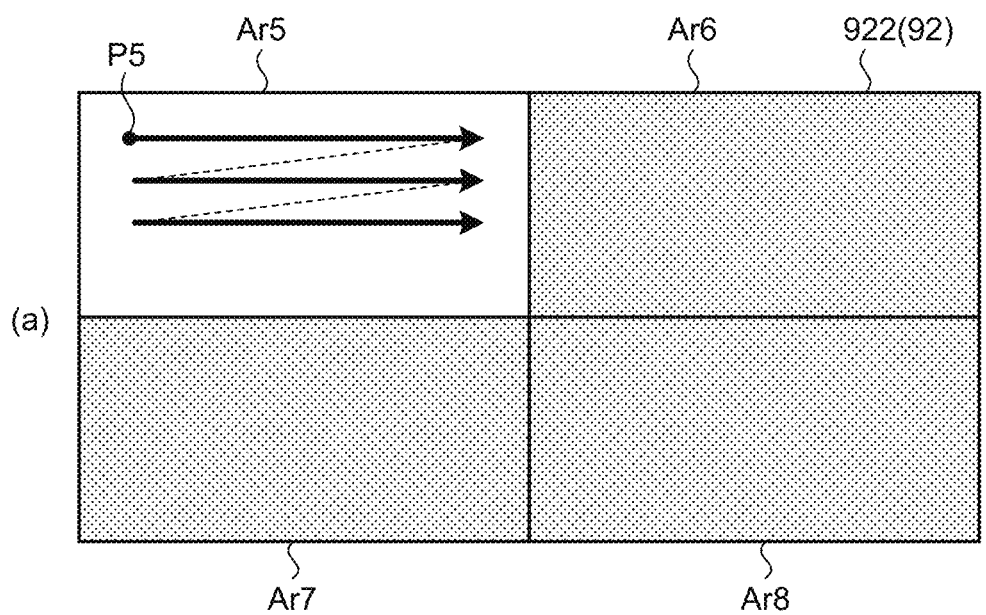
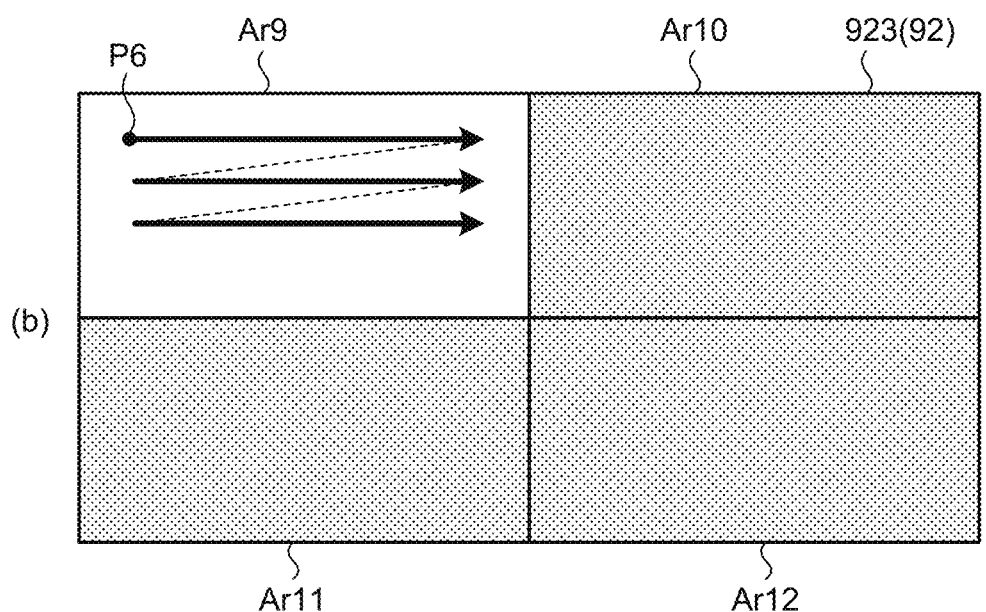

MEDICAL IMAGE PROCESSING APPARATUS AND MEDICAL OBSERVATION SYSTEM

FIELD

The present disclosure relates to a medical image processing apparatus and a medical observation system.

BACKGROUND

There has been conventionally known, for example, a medical image processing apparatus that quickly processes a captured image having a relatively large data amount such as the number of pixels of 4K or more (see, for example, Patent Literature 1).

In the medical image processing apparatus described in Patent Literature 1, a captured image is written into a specific memory area in a memory. Thereafter, in the medical image processing apparatus, a plurality of divided images obtained by dividing the captured image is read from a plurality of divided areas, in the above-described memory area, in which the plurality of divided images is written, respectively. Then, the medical image processing apparatus uses the same number of image processing units as the number of the divided images to execute image processing in parallel on the plurality of read divided images.

In addition, there has been conventionally known a medical image processing apparatus that acquires first and second captured images separately and generates a superimposed image by superimposing the first and second captured images of corresponding pixels (see, for example, Patent Literature 2).

Here, the first captured image is an image in which an observation target is irradiated with light in a first wavelength band, and light reflected by the observation target is captured by an image sensor. In addition, the second captured image is an image in which the observation target is irradiated with excitation light in a second wavelength band, which is different from the first wavelength band, and fluorescence from the observation target excited by the excitation light is captured by an image sensor.

CITATION LIST

Patent Literature

Patent Literature 1: JP 2018-79249 A
Patent Literature 2: US 2014/276008 A

SUMMARY

Technical Problem

By the way, in the medical image processing apparatus described in Patent Literature 2, for example, it is assumed that a first observation mode for observing an observation target with a first captured image and a second observation mode for observing the observation target with a superimposed image are provided. In this case, the following configuration is conceivable as a configuration that quickly processes the first captured image in the first observation mode and quickly processes the first and second captured images in the second observation mode.

That is, in order to process the first captured image, as in the medical image processing apparatus described in Patent Literature 1 described above, the above-described memory (hereinafter, described as a first memory) and the above-described plurality of image processing units (hereinafter, described as a plurality of first image processing units) are provided. Then, for the first captured image, the first memory and the plurality of first image processing units are used to divide the first captured image into a plurality of divided images and execute image processing in parallel. Moreover, in order to process the second captured image, a second memory, which is different from the first memory, and a plurality of second image processing units, which are different from the plurality of first image processing units, are provided. Then, for the second captured image, the second memory and the plurality of second image processing units are used to divide the second captured image into a plurality of divided images and execute image processing in parallel.

However, in a case where the second memory and the plurality of second image processing units are provided in addition to the first memory and the plurality of first image processing units, there is a problem in which the circuit scale increases.

Therefore, there is a demand for a technique capable of generating an image suitable for observation without increasing the circuit scale.

The present disclosure has been made in view of the above, and an object thereof is to provide a medical image processing apparatus and a medical observation system capable of generating an image suitable for observation without increasing a circuit scale.

Solution to Problem

To solve the above-describe problem and achieve the object, a medical image processing apparatus according to the present disclosure includes: a first captured image acquiring unit that acquires a first captured image obtained by capturing light from an observation target that emits fluorescence when irradiated with excitation light in a second wavelength band different from a first wavelength band and is irradiated with light in the first wavelength band; a second captured image acquiring unit that acquires a second captured image obtained by capturing the fluorescence from the observation target irradiated with the excitation light; a mode switching unit that switches between a first observation mode and a second observation mode; a memory that temporarily stores an image; a memory controller that controls writing of an image into the memory and reading of an image from the memory; and a plurality of image processing units that execute image processing in parallel on each input image, wherein the memory controller, in the first observation mode, writes the first captured image into a first memory area in the memory, reads a plurality of divided images obtained by dividing the first captured image into a number corresponding to the number of the image processing units from a plurality of divided areas in the first memory area, respectively, in which the plurality of divided images is written, respectively, and outputs the plurality of divided images to the plurality of image processing units, respectively, and in the second observation mode, writes the first captured image and the second captured image into a second memory area and a third memory area, respectively, each having a same memory capacity as a memory capacity of each of the divided areas in the memory, reads the first captured image and the second captured image from the second memory area and the third memory area, respectively, and outputs the first captured image and the second captured image into two image processing units of the plurality of image processing units, respectively.

Moreover, a medical observation system according to the present disclosure includes: a light source device that emits light in a first wavelength band and excitation light in a second wavelength band different from the first wavelength band; an imaging device that generates a first captured image by capturing light from an observation target that emits fluorescence when irradiated with the excitation light and is irradiated with light in the first wavelength band, and generates a second captured image by capturing the fluorescence from the observation target irradiated with the excitation light; and the medical image processing apparatus that processes the first captured image and the second captured image.

Advantageous Effects of Invention

According to the medical image processing apparatus and the medical observation system according to the present disclosure, it is possible to generate an image suitable for observation without increasing the circuit scale.

BRIEF DESCRIPTION OF DRAWINGS

FIG. 8 is a diagram for explaining operation of the memory controller in a fluorescence observation mode.

FIG. 9 is a diagram for explaining operation of the memory controller in the fluorescence observation mode.

DESCRIPTION OF EMBODIMENTS

Figure 1:
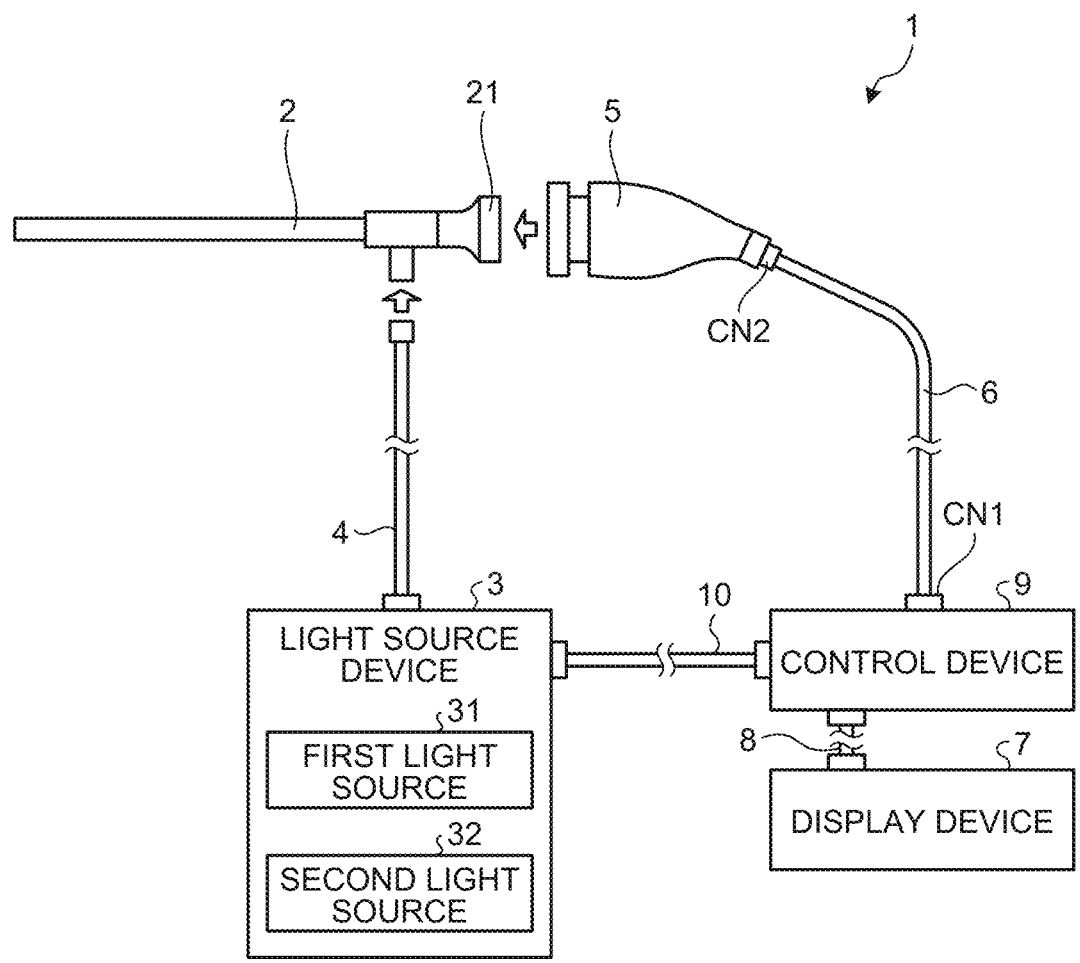
FIG. 1 is a diagram illustrating a configuration of a medical observation system according to an embodiment.

Hereinafter, embodiments for carrying out the present disclosure (hereinafter referred to as embodiments) will be described with reference to the drawings. Note that the present disclosure is not limited by the embodiments described below. Moreover, in the description of the drawings, the same parts are denoted by the same reference numerals.

[Schematic Configuration of Medical Observation System]

FIG. 1 is a diagram illustrating a configuration of a medical observation system 1 according to the present embodiment.

The medical observation system 1 is a system that is used in the medical field and captures an image of (observes) the inside of a living body (observation target), which is a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the present embodiment, the insertion unit 2 is constituted by a rigid endoscope. That is, the insertion unit 2 has an elongated shape, which is entirely rigid or partially flexible and partially rigid, and is inserted into a living body. An optical system that is constituted by one or a plurality of lenses and condenses light from a subject is provided in the insertion unit 2.

The light source device 3 is connected to one end of the light guide 4 and supplies light to the one end of the light guide 4 to irradiate the inside of a living body under the control of the control device 9. As illustrated in FIG. 1, the light source device 3 includes a first light source 31 and a second light source 32.

The first light source 31 emits light in a first wavelength band. In the present embodiment, the first light source 31 is constituted by a light emitting diode (LED) that emits white light (light in the first wavelength band).

The second light source 32 emits excitation light in a second wavelength band, which is different from the first wavelength band. In the present embodiment, the second light source 32 is constituted by a semiconductor laser that emits near-infrared excitation light in a near-infrared wavelength band (excitation light in the second wavelength band).

The near-infrared excitation light emitted by the second light source 32 is excitation light that excites a fluorescent substance such as indocyanine green. When excited by the near-infrared excitation light, the fluorescent substance such as indocyanine green emits fluorescence having its central wavelength on a long wavelength side of a central wavelength of the wavelength band of the near-infrared excitation light. Note that the wavelength band of the near-infrared excitation light and the wavelength band of the fluorescence may be set so as to partially overlap each other or may be set so as not to overlap each other at all.

In the light source device 3 according to the present embodiment, the first light source 31 is driven in a normal observation mode under the control of the control device 9. That is, in the normal observation mode, the light source device 3 emits normal light (white light). The normal observation mode corresponds to a first observation mode according to the present disclosure. On the other hand, in the light source device 3, under the control of the control device 9, in a fluorescence observation mode, the first light source 31 is driven in a first period and the second light source 32 is driven in a second period among the alternately repeated first and second periods. That is, in the fluorescence observation mode, the light source device 3 emits normal light (white light) in the first period and emits near-infrared excitation light in the second period. The fluorescence observation mode corresponds to a second observation mode according to the present disclosure.

Note that in the present embodiment, the light source device 3 is configured separately from the control device 9, but the present disclosure is not limited thereto, and a configuration in which the light source device 3 is provided inside the control device 9 may be adopted.

One end of the light guide 4 is detachably connected to the light source device 3, and the other end is detachably connected to the insertion unit 2. The light guide 4 transmits light (normal light and near-infrared excitation light) supplied from the light source device 3 from one end to the other end and supplies the light to the insertion unit 2. When the inside of a living body is irradiated with normal light (white light), the normal light reflected in the living body is condensed by the optical system in the insertion unit 2. Note that, hereinafter, for convenience of description, the normal light condensed by the optical system in the insertion unit 2 is described as a first subject image. In addition, in a case where the inside of the living body is irradiated with near-infrared excitation light, the near-infrared excitation light reflected in the living body and fluorescence emitted from a fluorescent substance such as indocyanine green after the fluorescent substance accumulating at a lesion in the living body is excited are condensed by the optical system in the insertion unit 2. Note that, hereinafter, for convenience of description, the near-infrared excitation light and the fluorescence condensed by the optical system in the insertion unit 2 are described as a second subject image.

The camera head 5 corresponds to an imaging device according to the present disclosure. The camera head 5 is detachably connected to a proximal end (eyepiece unit 21 (FIG. 1)) of the insertion unit 2. Under the control of the control device 9, the camera head 5 captures the first subject image (normal light) and the second subject image (near-infrared excitation light and fluorescence) condensed by the insertion unit 2 and outputs an image signal (RAW signal) obtained by capturing each of the images.

Note that a detailed configuration of the camera head 5 will be described later.

One end of the first transmission cable 6 is detachably connected to the control device 9 via a connector CN1 (FIG. 1), and the other end is detachably connected to the camera head 5 via a connector CN2 (FIG. 1). The first transmission cable 6 transmits an image signal and the like output from the camera head 5 to the control device 9 and transmits a control signal, a synchronization signal, a clock, power, and the like output from the control device 9 to the camera head 5.

Note that in the transmission of an image signal and the like from the camera head 5 to the control device 9 via the first transmission cable 6, the image signal and the like may be transmitted as an optical signal or may be transmitted as an electric signal. The same applies to transmission of a control signal, a synchronization signal, and a clock from the control device 9 to the camera head 5 via the first transmission cable 6.

The display device 7 is constituted by a display using liquid crystal, organic electro luminescence (EL), or the like and displays an image based on a video signal from the control device 9 under the control of the control device 9.

One end of the second transmission cable 8 is detachably connected to the display device 7, and the other end is detachably connected to the control device 9. The second transmission cable 8 transmits a video signal processed by the control device 9 to the display device 7.

The control device 9 corresponds to a medical image processing apparatus according to the present disclosure. The control device 9 is constituted by a central processing unit (CPU), a field-programmable gate array (FPGA), and the like and integrally controls operation of the light source device 3, the camera head 5, and the display device 7.

Note that a detailed configuration of the control device 9 will be described later.

One end of the third transmission cable 10 is detachably connected to the light source device 3, and the other end is detachably connected to the control device 9. The third transmission cable 10 transmits a control signal from the control device 9 to the light source device 3.

[Configuration of Camera Head]

Next, a configuration of the camera head 5 will be described.

Figure 2:
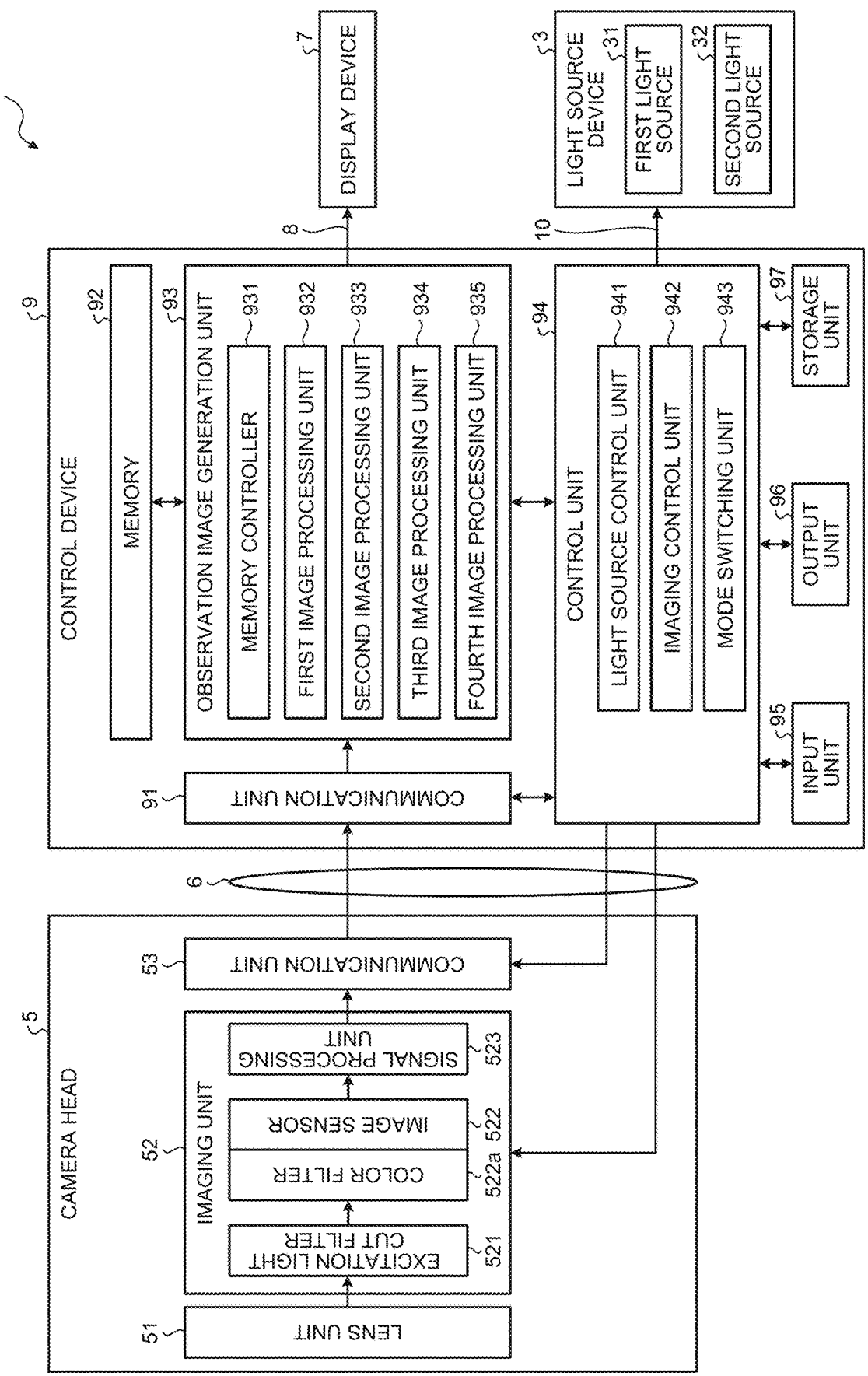
FIG. 2 is a block diagram illustrating a configuration of a camera head and a control device.

FIG. 2 is a block diagram illustrating a configuration of the camera head 5 and the control device 9.

Note that in FIG. 2, for convenience of description, the connectors CN1 and CN2 between the control device 9 and the camera head 5, and the first transmission cable 6, connectors between the control device 9 and the display device 7, and the second transmission cable 8, and connectors between the control device 9 and the light source device 3, and the third transmission cable 10 are omitted.

As illustrated in FIG. 2, the camera head 5 includes a lens unit 51, an imaging unit 52, and a communication unit 53.

The lens unit 51 includes one or a plurality of lenses and forms the first subject image (normal light) and the second subject image (near-infrared excitation light and fluorescence) condensed by the insertion unit 2 on an imaging surface of the imaging unit 52 (image sensor 522).

The imaging unit 52 captures an image of the inside of the living body under the control of the control device 9. As illustrated in FIG. 2, the imaging unit 52 includes an excitation light cut filter 521, the image sensor 522, and a signal processing unit 523.

The excitation light cut filter 521 is provided between the lens unit 51 and the image sensor 522 and is constituted by a band stop filter that removes a specific wavelength band. Note that, hereinafter, for convenience of description, a wavelength band that is cut (removed) by the excitation light cut filter 521 is described as a cut band, a wavelength band that is on a short wavelength side of the cut band and passes through the excitation light cut filter 521 is described as a short wavelength side transmission band, and a wavelength band that is on a long wavelength side of the cut band and passes through the excitation light cut filter 521 is described as a long wavelength side transmission band.

Here, the cut band includes at least a part of the wavelength band of the near-infrared excitation light. In the present embodiment, the cut band includes a part of the wavelength band of the near-infrared excitation light. In addition, the long wavelength side transmission band includes a part of the wavelength band of the near-infrared excitation light and the wavelength band of the fluorescence. Moreover, the short wavelength side transmission band includes a wavelength band (the first wavelength band) of the normal light (white light).

That is, the excitation light cut filter 521 transmits the first subject image (normal light (white light)) directed from the lens unit 51 to the image sensor 522. On the other hand, the excitation light cut filter 521 transmits a part of the near-infrared excitation light and the fluorescence of the second subject image (near-infrared excitation light and fluorescence) directed from the lens unit 51 to the image sensor 522.

The image sensor 522 is constituted by a charge coupled device (CCD), a complementary metal oxide semiconductor (CMOS), or the like that receives light that has passed through the excitation light cut filter 521 and converts the light into an electric signal (analog signal).

Here, the imaging surface (light receiving surface) of the image sensor 522 is provided with a color filter 522*a* (FIG. 2) in which three filter groups grouped according to a wavelength band of light (R (red), G (green), and B (blue)) to be transmitted are arranged in a predetermined format (for example, a Bayer array).

Specifically, the color filter 522*a* includes an R filter group that mainly transmits light in an R wavelength band, a B filter group that mainly transmits light in a B wavelength band, and a G filter group that mainly transmits light in a G wavelength band.

Note that the R, G, and B filter groups also transmit near-infrared excitation light and fluorescence. In addition, the image sensor 522 is sensitive not only to light in R, G, and B wavelength bands but also to light in near-infrared excitation light and fluorescence wavelength bands.

The image sensor 522 captures the first subject image (normal light) at a predetermined frame rate in the normal observation mode under the control of the control device 9. Furthermore, under the control of the control device 9, the image sensor 522 captures images every first and second periods that are alternately repeated in synchronization with a light emission timing of the light source device 3 in the fluorescence observation mode.

Hereinafter, for convenience of description, an image generated by capturing the first subject image (normal light) by the image sensor 522 is described as a normal light image (corresponding to a first captured image according to the present disclosure). In addition, an image generated by capturing the second subject image (near-infrared excitation light and fluorescence) by the image sensor 522 is described as a fluorescence image (corresponding to a second captured image according to the present disclosure). In addition, the normal light image and the fluorescence image are collectively described as a captured image.

Under the control of the control device 9, the signal processing unit 523 performs signal processing on a captured image (analog signal) generated by the image sensor 522 and outputs the captured image (RAW signal (digital signal)).

Here, examples of the signal processing performed by the signal processing unit 523 include A/D conversion and thinning processing.

The thinning processing is processing for, in a case where the total number of pixels of the captured image generated by the image sensor 522 is set to a first number of pixels, setting the total number of pixels of the captured image to a second number of pixels, which is equal to or less than 1/N (equal to or less than 2/N in each of vertical and horizontal directions) of the first number of pixels. That is, for example, by the thinning processing, a captured image having the number of pixels of 4K is converted into a captured image having the number of pixels of full high definition (HD) or less. Note that, in the thinning processing, the total number of pixels of the captured image may be set to the second number of pixels by deleting, at a constant cycle, pixels of the captured image whose total number of pixels is the first number of pixels, or the total number of pixels of the captured image may be set to the second number of pixels by adding adjacent pixels in the captured image whose total number of pixels is the first number of pixels.

Figure 3:
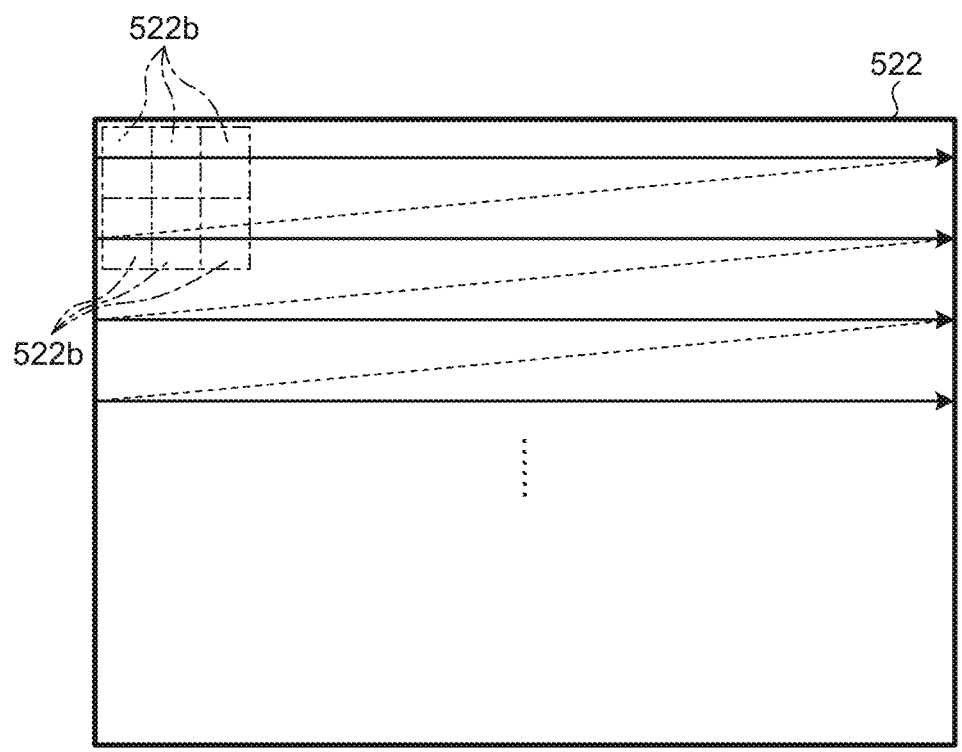
FIG. 3 is a diagram for explaining a captured image output from an imaging unit.

FIG. 3 is a diagram for explaining a captured image output from the imaging unit 52. Specifically, FIG. 3 is a diagram schematically illustrating physical arrangement of pixels 522*b* in the image sensor 522.

Note that, in FIG. 3, for convenience of description, only some pixels 522*b* among all the pixels in the image sensor 522 are illustrated.

The imaging unit 52 sequentially outputs the captured image in raster units. Specifically, in the image sensor 522, each of the pixels 522*b* is arranged in a matrix. As indicated by arrows and broken lines in FIG. 3, in each of the pixels 522*b* in the first row, the imaging unit 52 sequentially outputs, from each of the pixels 522*b*, the image for one line from the pixel 522*b* arranged in the first column to the pixel 522*b* arranged in the last column. Note that one arrow illustrated in FIG. 3 indicates the image for one line. Subsequently, in each of the pixels 522*b* in the second row, the imaging unit 52 sequentially outputs, from each of the pixels 522*b*, the image for one line from the pixel 522*b* arranged in the first column to the pixel 522*b* arranged in the last column. Then, the imaging unit 52 outputs the captured image for one frame by continuing the above processing up to the last line. When outputting the captured image for the next frame, the imaging unit 52 returns to each of the pixels 522*b* of the first row and performs the same processing as described above.

Note that, in the above description, raster output of the captured image in a case where the above-described thinning processing is not performed has been described. However, even in a case where the above-described thinning processing is performed, the captured image after the thinning processing is sequentially output in raster units in the order indicated by the arrows and broken lines in FIG. 3.

The communication unit 53 functions as a transmitter that transmits the captured image in raster units sequentially output from the imaging unit 52 to the control device 9 via the first transmission cable 6. The communication unit 53 is constituted by, for example, a high-speed serial interface that communicates a captured image with the control device 9 via the first transmission cable 6 at a transmission rate of 1 Gbps or more.

[Configuration of Control Device]

Next, a configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives the captured image in raster units sequentially output from the camera head 5 (communication unit 53) via the first transmission cable 6. The communication unit 91 is constituted by, for example, a high-speed serial interface that communicates a captured image with the communication unit 53 at a transmission rate of 1 Gbps or more. That is, the communication unit 91 corresponds to a first captured image acquiring unit and a second captured image acquiring unit according to the present disclosure.

The memory 92 is constituted by, for example, a dynamic random access memory (DRAM) or the like. The memory 92 temporarily stores the captured image in raster units sequentially output from the camera head 5 (communication unit 53) for a plurality of frames.

The observation image generation unit 93 processes the captured image in raster units sequentially output from the camera head 5 (communication unit 53) and received by the communication unit 91 under the control of the control unit 94. As illustrated in FIG. 2, the observation image generation unit 93 includes a memory controller 931 and first to fourth image processing units 932 to 935.

The memory controller 931 controls writing of an image into the memory 92 and reading of an image from the memory 92 under the control of the control unit 94. Note that details of the function of the memory controller 931 will be described in "Operation of Control Device" described later.

The first to fourth image processing units 932 to 935 execute image processing in parallel on each input image under the control of the control unit 94.

Figure 4:
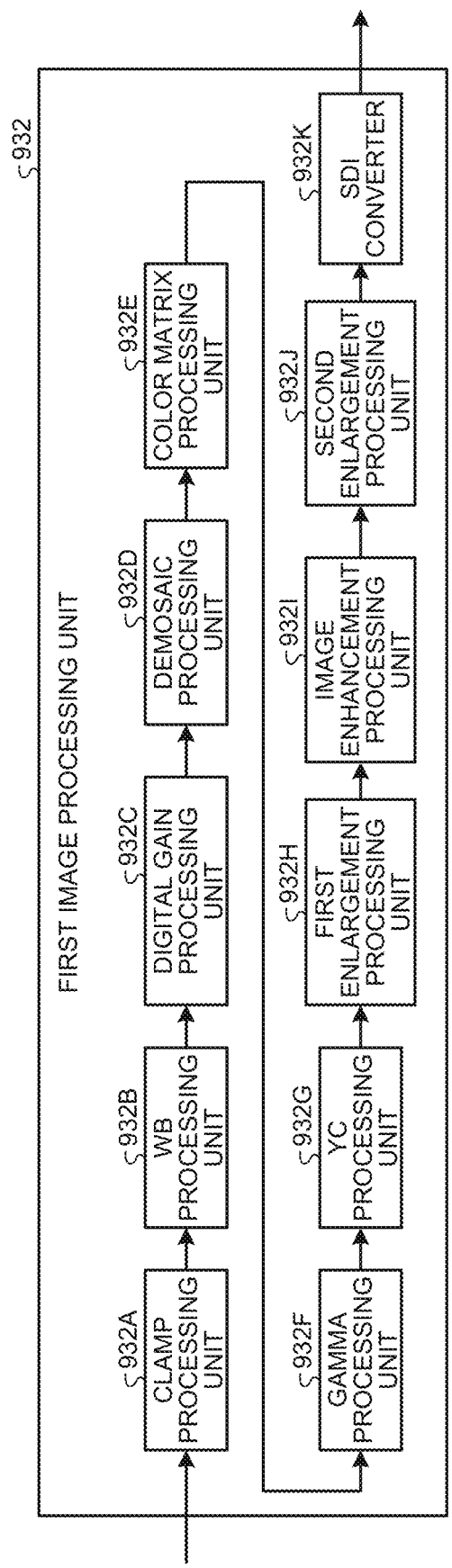
FIG. 4 is a block diagram illustrating a configuration of a first image processing unit.

FIG. 4 is a block diagram illustrating a configuration of the first image processing unit 932.

Note that configurations of the first to fourth image processing units 932 to 935 are the same. Therefore, only the configuration of the first image processing unit 932 will be described below.

As illustrated in FIG. 4, the first image processing unit 932 includes a clamp processing unit 932A, a WB processing unit 932B, a digital gain processing unit 932C, a demosaic processing unit 932D, a color matrix processing unit 932E, a gamma processing unit 932F, a YC processing unit 932G, a first enlargement processing unit 932H, an image enhancement processing unit 932I, a second enlargement processing unit 932J, and a serial digital interface (SDI) converter 932K.

Here, images input to the first to fourth image processing units 932 to 935 (images corresponding to the captured images (RAW data) output from the camera head 5) include, for each pixel, component information (pixel data) of any one of R, G, and B corresponding the filter groups of R, G, and B constituting the color filter 522a. Hereinafter, for convenience of description, the component information of R is described as an r value, the component information of G is described as a g value, and the component information of B is described as a b value.

The clamp processing unit 932A executes clamp processing for fixing the black level to an input image.

The WB processing unit 932B executes WB processing (white balance adjustment processing) for multiplying each of the r value, the g value, and the b value in the image after the clamp processing by a specific gain.

The digital gain processing unit 932C executes digital gain processing for multiplying the r value, the g value, and the b value in the image after the WB processing by a digital gain to amplify the r value, the g value, and the b value.

The demosaic processing unit 932D executes demosaic processing for giving pixel values (R (r value), G (g value), B (b value)) of the r value, the g value, and the b value to the image after the digital gain processing by interpolation for each pixel.

The color matrix processing unit 932E executes color matrix processing for correcting the pixel value (R, G, and B) for each pixel to a pixel value (Rm, Gm, and Bm) by using a color correction matrix on the image after the demosaic processing.

The gamma processing unit 932F executes gamma processing (f correction) on the image after the color matrix processing.

The YC processing unit 932G executes YC conversion for converting the image after the gamma processing into a luminance signal and a chrominance signal (Y, $C_B/C_R$ signal).

The first enlargement processing unit 932H executes first enlargement processing (electronic zoom) on the image after the YC conversion.

The image enhancement processing unit 932I executes image enhancement processing on the image after the first enlargement processing (electronic zoom).

The second enlargement processing unit 932J executes second enlargement processing (electronic zoom) on the image after the image enhancement processing.

The SDI converter 932K executes SDI conversion on the image after the second enlargement processing (electronic zoom).

Then, the image from each of the SDI converters 932K in the first to fourth image processing units 932 to 935 is output to the display device 7 as a first video signal or a second video signal, which will be described later, via the second transmission cable 8.

The control unit 94 is composed using, for example, a CPU, an FPGA, or the like, and outputs a control signal via the first to third transmission cables 6, 8, and 10, thereby controlling the operation of the light source device 3, the camera head 5, and the display device 7 and controlling the entire operation of the control device 9. As illustrated in FIG. 2, the control unit 94 includes a light source control unit 941, an imaging control unit 942, and a mode switching unit 943. Note that the functions of the light source control unit 941, the imaging control unit 942, and the mode switching unit 943 will be described in "Operation of Control Device" described later.

The input unit 95 is composed using an operation device such as a mouse, a keyboard, and a touch panel and receives a user operation by a user such as a doctor. Then, the input unit 95 outputs an operation signal corresponding to the user operation to the control unit 94.

The output unit 96 is composed using a speaker, a printer, or the like and outputs various types of information.

The storage unit 97 stores a program executed by the control unit 94, information necessary for processing of the control unit 94, and the like.

[Operation of Control Device]

Next, operation of the control device 9 described above will be described.

Figure 5:
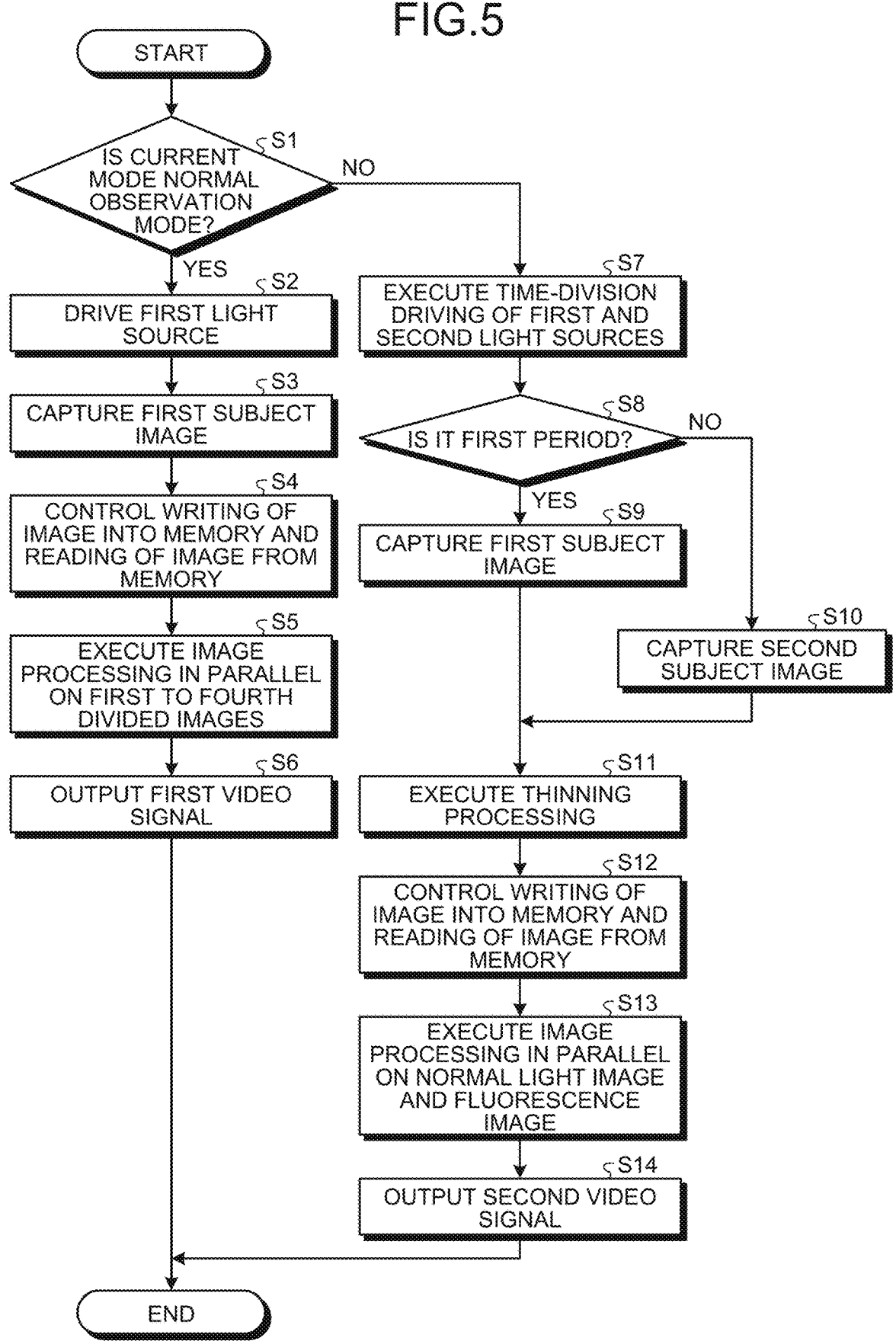
FIG. 5 is a flowchart illustrating operation of the control device.

FIG. 5 is a flowchart illustrating the operation of the control device 9.

Note that, in the following description, it is assumed that the image sensor 522 is an image sensor that generates a captured image having the number of pixels of 4K. In addition, it is assumed that the maximum data amount that can be processed by the first image processing unit 932 is the data amount of the image having the number of pixels of HD. The same applies to the second to fourth image processing units 933 to 935.

First, the control unit 94 determines whether the current mode of the control device 9 is the normal observation mode (step S1).

Note that the mode of the control device 9 is switched by the mode switching unit 943. Specifically, the mode switching unit 943 switches the mode of the control device 9 to the normal observation mode or the fluorescence observation mode in response to a user operation on the input unit 95 by a user such as a doctor.

When it is determined that the mode is the normal observation mode (step S1: Yes), the light source control unit 941 drives the first light source 31 (step S2). That is, the inside of the living body is irradiated with normal light (white light).

After step S2, the imaging control unit 942 causes the image sensor 522 to capture the first subject image (normal light) at a predetermined frame rate (step S3). Then, the imaging unit 52 sequentially outputs the normal light image having the number of pixels of 4K in raster units.

After step S3, the memory controller 931 controls writing of the image into the memory 92 and reading of the image from the memory 92 (step S4).

Figure 6:
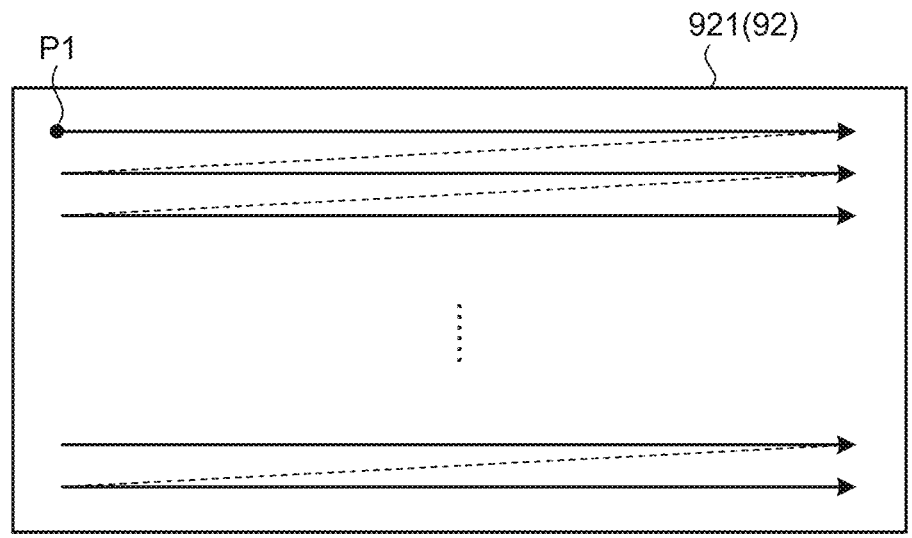
FIG. 6 is a diagram for explaining operation of a memory controller in a normal observation mode.
Figure 7:
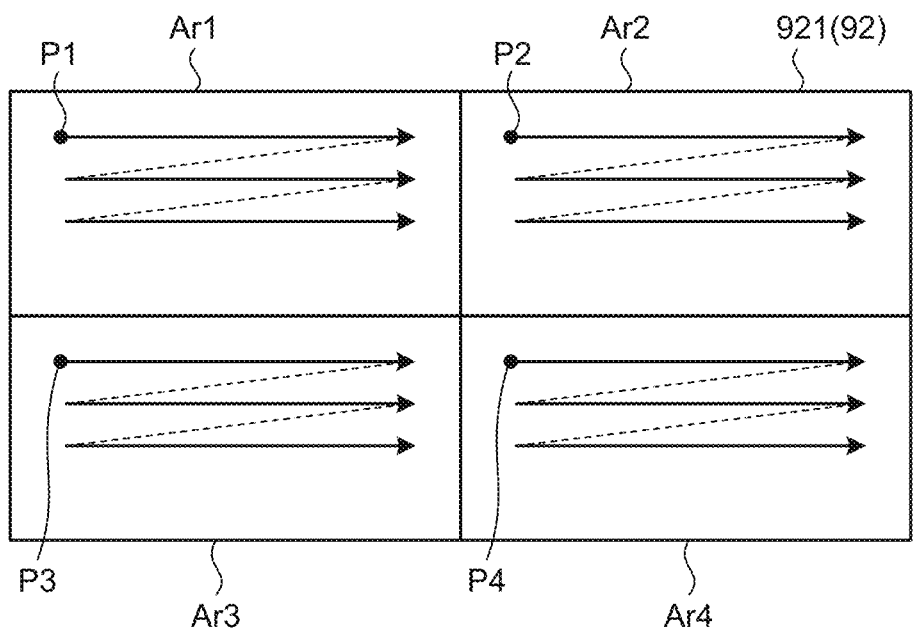
FIG. 7 is a diagram for explaining operation of the memory controller in the normal observation mode.

FIGS. 6 and 7 are diagrams for explaining operation of the memory controller 931 in the normal observation mode. Specifically, FIG. 6 is a diagram for explaining writing of the normal light image into the memory 92. FIG. 7 is a diagram for explaining reading of the normal light image from the memory 92. Note that FIGS. 6 and 7 schematically illustrate a specific bank 921 among a plurality of banks in the memory 92. The bank 921 corresponds to a first memory area according to the present disclosure and has a memory capacity corresponding to the data amount of an image having the number of pixels of 4K in the present embodiment. In addition, in FIG. 7, the entire area of the bank 921 is equally divided into four areas, which are first to fourth divided areas Ar1 to Ar4, in a square lattice shape. That is, in the present embodiment, the first to fourth divided areas Ar1 to Ar4 each have a memory capacity corresponding to the data amount of an image having the number of pixels of HD.

Specifically, as indicated by arrows and broken lines in FIG. 6, the memory controller 931 sequentially writes, into the bank 921, the normal light image (the number of pixels: 4K) in raster units sequentially output from the imaging unit 52 and received by the communication unit 91 line by line. Note that one arrow illustrated in FIG. 6 indicates the image for one line in the normal light image (the number of pixels: 4K).

In addition, the memory controller 931 sequentially reads the image written into each of the first to fourth divided areas Ar1 to Ar4 from first to fourth storage positions P1 to P4 line by line as indicated by arrows and broken lines in FIG. 7 substantially at the same time as the timing of writing the normal light image (the number of pixels: 4K) of one frame to the fourth storage position P4 (FIG. 7).

Note that the image (hereinafter, described as a first divided image) written into the first divided area Ar1 is an image of a rectangular area including the upper left corner position in the normal light image. The pixel data stored at the first storage position P1 is the pixel data of the pixel at the upper left corner position in the first divided image. In addition, an image (hereinafter, described as a second divided image) written into the second divided area Ar2 is an image of a rectangular area including the upper right corner position in the normal light image. The pixel data stored at the second storage position P2 is the pixel data of the pixel at the upper left corner position in the second divided image. Moreover, an image (hereinafter, described as a third divided image) written into the third divided area Ar3 is an image of a rectangular area including the lower left corner position in the normal light image. The pixel data stored at the third storage position P3 is the pixel data of the pixel at the upper left corner position in the third divided image. Furthermore, an image (hereinafter, described as a fourth divided image) written into the fourth divided area Ar4 is an image of a rectangular area including the lower right corner position in the normal light image. The pixel data stored at the fourth storage position P4 is the pixel data of the pixel at the upper left corner position in the fourth divided image.

Since the first to fourth divided images described above are images obtained by equally dividing the normal light image having the number of pixels of 4K into four, the first to fourth divided images are images having the number of pixels of HD.

Then, the read first to fourth divided images (the number of pixels: HD) are sequentially input to the first to fourth image processing units 932 to 935, respectively, line by line. Note that one arrow illustrated in FIG. 7 indicates the image for one line in the first to fourth divided images (the number of pixels: HD).

After step S4, the first to fourth image processing units 932 to 935 execute image processing in parallel on the input first to fourth divided images (the number of pixels: HD) (step S5). Here, the first to fourth image processing units 932 to 935 execute first image processing. Note that the first image processing will be described in "First and Second Image Processing" described later.

After step S5, the observation image generation unit 93 outputs the first video signal for displaying the normal light image (the number of pixels: 4K), which is obtained by combining the first to fourth divided images after the execution of the first image processing, to the display device 7 via the second transmission cable 8 (step S6). Consequently, the display device 7 displays the normal light image (the number of pixels: 4K) based on the first video signal.

Returning to step S1, when it is determined that the current mode is the fluorescence observation mode (step S1: No), the light source control unit 941 executes time-division driving of the first and second light sources 31 and 32 (step S7). Specifically, in step S7, the light source control unit 941 causes the first light source 31 to emit light in the first period and causes the second light source 32 to emit light in the second period among the alternately repeated first and second periods based on a synchronization signal.

After step S7, the imaging control unit 942 causes the imaging unit 52 to capture the first and second subject images in the first and second periods, respectively, in synchronization with the light emission timings of the first and second light sources 31 and 32 based on the synchronization signal (steps S8 to S11). That is, in a case where it is the first period (step S8: Yes), in other words, in a case where the inside of the living body is irradiated with the normal light (white light), the image sensor 522 captures the first subject image (normal light) to generate the normal light image (step S9). On the other hand, in a case where it is the second period (step S8: No), in other words, in a case where the inside of the living body is irradiated with the near-infrared excitation light, the image sensor 522 captures the second subject image (the near-infrared excitation light and the fluorescence) to generate the fluorescence image (step S10). Furthermore, the signal processing unit 523 executes the thinning processing (step S11). By the thinning processing, the normal light image and the fluorescence image having the number of pixels of 4K are set to the normal light image and the fluorescence image having the number of pixels of HD, respectively.

Then, the imaging unit 52 sequentially outputs the normal light image having the number of pixels HD in raster units, the normal light image being obtained by capturing the first subject image in the first period, and sequentially outputs the fluorescence image having the number of pixels HD in raster units, the fluorescence image being obtained by capturing the second subject image in the second period.

After step S11, the memory controller 931 controls writing of the image into the memory 92 and reading of the image from the memory 92 (step S12).

FIGS. 8 and 9 are diagrams for explaining operation of the memory controller 931 in the fluorescence observation mode. Specifically, FIG. 8(a) is a diagram for explaining writing of the normal light image into the memory 92. FIG. 8(b) is a diagram for explaining writing of the fluorescence image into the memory 92. FIG. 9(a) is a diagram for explaining reading of the normal light image from the memory 92. FIG. 9(b) is a diagram for explaining reading of the fluorescence image from the memory 92. Note that FIGS. 8 and 9 schematically illustrate specific banks 922 and 923 among the plurality of banks in the memory 92. The banks 922 and 923 each have the same memory capacity as that of the bank 921 (in the present embodiment, memory capacity corresponding to the data amount of an image having the number of pixels of 4K). In addition, in FIGS. 8 and 9, the entire area of the bank 922 is equally divided into four areas, which are fifth to eighth divided areas Ar5 to Ar8, in a square lattice shape, and the entire area of the bank 923 is equally divided into four areas, which are ninth to 12th divided areas Ar9 to Ar12, in a square lattice shape. That is, each of the fifth to 12th divided areas Ar5 to Ar12 has the same memory capacity as that of each of the first to fourth divided areas Ar1 to Ar4 (in the present embodiment, the memory capacity corresponding to the data amount of the image having the number of pixels of HD). Note that the fifth divided area Ar5 in the bank 922 corresponds to a second memory area according to the present disclosure. In addition, the ninth divided area Ar9 in the bank 923 corresponds to a third memory area according to the present disclosure.

Specifically, as indicated by arrows and broken lines in FIG. 8(a), the memory controller 931 sequentially writes, into the fifth divided area Ar5 in the bank 922, the normal light image (the number of pixels: HD) in raster units sequentially output from the imaging unit 52 and received by the communication unit 91 line by line. Note that one arrow illustrated in FIG. 8(a) indicates the image for one line in the normal light image (the number of pixels: HD). In addition, as indicated by arrows and broken lines in FIG. 8(b), after writing the normal light image (the number of pixels: HD) of one frame into the bank 922, the memory controller 931 sequentially writes, into the ninth divided area Ar9 in the bank 923, the fluorescence image (the number of pixels: HD) in raster units sequentially output from the imaging unit 52 and received by the communication unit 91 line by line. Note that one arrow illustrated in FIG. 8(b) indicates the image for one line in the fluorescence image (number of pixels: HD).

In addition, the memory controller 931 sequentially reads the normal light image (the number of pixels: HD) and the fluorescence image (the number of pixels: HD) written into the fifth and ninth divided areas Ar5 and Ar9, respectively, from the fifth and sixth storage positions P5 and P6 line by line, as indicated by arrows and broken lines in FIG. 9, substantially at the same time as the timing of starting writing the fluorescence image (the number of pixels: HD) from the sixth storage position P6. Note that one arrow illustrated in FIG. 9 indicates the image for one line in the normal light image (the number of pixels: HD) and the fluorescence image (the number of pixels: HD). In addition, in FIGS. 8 and 9, arrows at the temporally same timing have the same thickness. That is, the arrows illustrated in FIGS. 8(b), 9(a), and 9(b) have the same thickness and have a thickness different from the thickness of the arrows illustrated in FIG. 8(a). Here, the pixel data stored at the fifth storage position P5 is the pixel data of the pixel at the upper left corner position in the normal light image (the number of pixels: HD). In addition, the pixel data stored at the sixth storage position P6 is the pixel data of the pixel at the upper left corner position in the fluorescence image (the number of pixels: HD).

The read normal light image (the number of pixels: HD) and fluorescence image (the number of pixels: HD) are sequentially input to the first and second image processing units 932 and 933, respectively, line by line. Note that the third and fourth image processing units 934 and 935 do not execute any processing in the fluorescence observation mode.

After step S12, the first and second image processing units 932 and 933 execute image processing in parallel on the input normal light image (the number of pixels: HD) and fluorescence image (the number of pixels: HD) (step S13). Here, the first image processing unit 932 executes the first image processing on the input normal light image (the number of pixels: HD). On the other hand, the second image processing unit 933 executes the second image processing on the input fluorescence image (the number of pixels: HD). Note that the first and second image processing will be described in "First and Second Image Processing" described later.

After step S13, the observation image generation unit 93 outputs the second video signal, to the display device 7 via the second transmission cable 8, for displaying at least one of the normal light image after the first image processing is executed, the fluorescence image after the second image processing is executed, and a superimposed image in which the normal light image and the fluorescence image are superimposed according to corresponding pixels (step S14). Consequently, the display device 7 displays the image (the number of pixels: 4K) based on the second video signal.

[First and Second Image Processing]

In the first and second image processing, under the control of the control unit 94, for example, the clamp processing, the WB processing, the digital gain processing, the demosaic processing, the color matrix processing, the gamma processing, the YC processing, the first enlargement processing, and the image enhancement processing are executed as follows.

(1) Clamp Processing

In the first and second image processing, the same clamp processing is executed.

(2) WB Processing

In the first and second image processing, different gains are used in the WB processing.

Specifically, in the first image processing, in the WB processing, the r value, the g value, and the b value in any one of the first to fourth divided images (the number of pixels: HD) or the normal light image (the number of pixels: HD) after the clamp processing are multiplied by three first gains, respectively. The three first gains are gains for white balancing the r value, the g value, and the b value in the wavelength band of the normal light (white light).

On the other hand, in the second image processing, in the WB processing, the r value, the g value, and the b value in the fluorescence image (the number of pixels: HD) after the clamp processing are multiplied by three second gains, respectively. Here, since sensitivity to fluorescence in the image sensor 522 is substantially the same in R, G, and B, the three second gains have substantially the same values.

(3) Digital Gain Processing

In the first and second image processing, in the digital gain processing, different digital gains are used. That is, in the first image processing, in the digital gain processing, a first digital gain is used. On the other hand, in the second image processing, in the digital gain processing, a second digital gain, which is different from the first digital gain, is used.

Specifically, in the second image processing, in the digital gain processing, since the brightness of the fluorescence image is low, the r value, the g value, and the b value in the fluorescence image (the number of pixels: HD) after the WB processing are multiplied by digital gains common to all the pixels so that the fluorescence image have the same brightness as the normal light image.

(4) Demosaic Processing

In the second image processing, the demosaic processing need not be executed.

(5) Color Matrix Processing

In the first image processing, the color matrix processing is executed.

On the other hand, in the second image processing, since the fluorescence image has no color, the color matrix processing is not executed. Alternatively, in the second image processing, the color matrix processing is executed using a color correction matrix that does not correct a color.

(6) Gamma Processing

In the second image processing, γ correction with higher contrast than the first image processing is executed.

(7) YC Conversion

In the second image processing, chrominance values (a Cb value and a Cr value) of the luminance signal and the chrominance signal after the YC conversion are set to 0 (a black-and-white image). Alternatively, in the second image processing, coloring may be performed by adding a small chrominance value.

(8) First Enlargement Processing

In the first and second image processing, in the first enlargement processing, the same electronic zoom magnification may be used, or a different electronic zoom magnification may be used.

(9) Image Enhancement Processing

In the first and second image processing, the intensity of enhancing an image is different in the image enhancement processing. That is, in the first image processing, first intensity is set as the intensity. On the other hand, in the second image processing, second intensity, which is different from the first intensity, is set as the intensity.

Here, in the second image processing, since the fluorescence image is dark and contains noise, the intensity of image enhancement (the second intensity) may be lower than the intensity of image enhancement (the first intensity) in the first image processing. Moreover, in the second image processing, noise reduction processing may be additionally executed.

According to the embodiment described above, the following effects are obtained.

In the normal observation mode, the control device 9 according to the present embodiment divides the normal light image (the number of pixels: 4K) into the first to fourth divided images using the memory 92 and the first to fourth image processing units 932 to 935 and executes the image processing in parallel. On the other hand, in the fluorescence observation mode, the control device 9 executes image processing on the normal light image (the number of pixels: HD) and the fluorescence image (the number of pixels: HD) in parallel using the memory 92 and the first and second image processing units 932 and 933.

That is, it is not necessary to separately provide a memory and a plurality of image processing units corresponding to the normal light image and the fluorescence image, and it is possible to execute the normal observation mode and the fluorescence observation mode only by providing the single memory 92 and the four image processing units 932 to 935.

Therefore, it is possible to generate an image suitable for observation without increasing the circuit scale.

OTHER EMBODIMENTS

Although the embodiment for carrying out the present disclosure has been described so far, the present disclosure should not be limited only by the above-described embodiment.

In the above-described embodiment, the number of image processing units according to the present disclosure is four, but the present disclosure is not limited thereto, and other numbers of image processing units may be provided. For example, in a case where a normal light image having the number of pixels of 8K is processed in the normal observation mode, if an image processing unit of which the maximum data amount that can be processed is a data amount of an HD image is used similarly to the above-described embodiment, it is necessary to provide 16 image processing units.

In the above-described embodiment, in a case where the image sensor 522 is an image sensor that generates an HD captured image, processing may be performed as follows.

For example, in the normal observation mode, after step S3, the signal processing unit 523 enlarges the number of pixels of a normal light image (the number of pixels: HD) to 4K under the control of the imaging control unit 942. Then, the memory controller 931 stores the normal light image (the number of pixels: 4K) into the bank 921. Thereafter, the control device 9 executes processing (steps S4 to S6) similar to the above-described embodiment. On the other hand, in the fluorescence observation mode, the control device 9 does not execute only step S11 among steps S7 to S14 described in the above-described embodiment.

In the above-described embodiment, in the fluorescence observation mode, the light in the first wavelength band and the excitation light in the second wavelength band are emitted in a time division manner, but the present disclosure is not limited thereto. For example, the light in the first wavelength band and the excitation light in the second wavelength band may be simultaneously emitted, the light in the first wavelength band and the excitation light and the fluorescence in the second wavelength band may be separated by a filter on a side of capturing an image and may be separately captured by two image sensors.

In the above-described embodiment, the light in the first wavelength band is white light, and the excitation light in the second wavelength band is near-infrared excitation light, but the present disclosure is not limited thereto. As the first and second light sources 31 and 32 having first and second wavelength bands, which are different from each other, other configurations may be adopted as long as the first light source 31 emits light in first wavelength band and the second light source 32 emits light in the second wavelength band, which is different from the first wavelength band. At this time, the first and second wavelength bands may be wavelength bands that partially overlap or that do not overlap at all. In addition, the first light source 31 may emit narrow band light.

By the way, photodynamic diagnosis (PDD), which is one of cancer diagnostic methods for detecting cancer cells, is conventionally known.

In the photodynamic diagnosis, for example, a photosensitive substance such as 5-aminolevulinic acid (hereinafter, described as 5-ALA) is used. The 5-ALA is a natural amino acid originally contained in living bodies of animals and plants. The 5-ALA is taken up into cells after administration in vivo and is biosynthesized into protoporphyrin in mitochondria. In cancer cells, the protoporphyrin excessively accumulates. In addition, the protoporphyrin that excessively accumulates in the cancer cells is photoactive. Therefore, when the protoporphyrin is excited by excitation light (for example, blue visible light in a wavelength band of 375 nm to 445 nm), the protoporphyrin emits fluorescence (for example, red fluorescence in a wavelength band of 600 nm to 740 nm). As described above, a cancer diagnostic method that makes cancer cells fluorescently emit light using a photosensitive substance is referred to as photodynamic diagnosis.

In the above-described embodiment, the first light source 31 may be constituted by an LED that emits white light, and the second light source 32 may be constituted by a semiconductor laser that emits excitation light for exciting protoporphyrin (for example, blue visible light in a wavelength band of 375 nm to 445 nm). Even in such a configuration, the same effects as those of the above-described embodiment can be obtained.

In the above-described embodiment, the first and second periods are set to be alternately repeated in the fluorescence observation mode, but the present disclosure is not limited thereto, and at least one of the first and second periods may be continuous, and the ratio of the frequencies of the first and second periods may be a ratio other than 1:1.

In the above-described embodiment, the medical image processing apparatus according to the present disclosure is mounted on the medical observation system 1, in which the insertion unit 2 is constituted by a rigid endoscope, but the present disclosure is not limited thereto. For example, the medical image processing apparatus according to the present disclosure may be mounted on a medical observation system, in which the insertion unit 2 is constituted by a flexible endoscope. Moreover, the medical image processing apparatus according to the present disclosure may be mounted on a medical observation system such as a surgical microscope (see, for example, JP 2016-42981 A) that enlarges and observes a predetermined field of view in a subject (in a living body) or a subject surface (living body surface).

In the above-described embodiment, a part of the configuration of the camera head 5 or a part of the configuration of the control device 9 may be provided in, for example, the connector CN1 or the connector CN2.

REFERENCE SIGNS LIST

1 MEDICAL OBSERVATION SYSTEM
2 INSERTION UNIT
3 LIGHT SOURCE DEVICE
4 LIGHT GUIDE
5 CAMERA HEAD
6 FIRST TRANSMISSION CABLE
7 DISPLAY DEVICE
8 SECOND TRANSMISSION CABLE
9 CONTROL DEVICE
10 THIRD TRANSMISSION CABLE
21 EYEPIECE UNIT
31 FIRST LIGHT SOURCE
32 SECOND LIGHT SOURCE
51 LENS UNIT
52 IMAGING UNIT
53 COMMUNICATION UNIT
91 COMMUNICATION UNIT
92 MEMORY
93 OBSERVATION IMAGE GENERATION UNIT
94 CONTROL UNIT
95 INPUT UNIT
96 OUTPUT UNIT
97 STORAGE UNIT
521 EXCITATION LIGHT CUT FILTER
522 IMAGE SENSOR
522a COLOR FILTER
523 SIGNAL PROCESSING UNIT
921 to 923 BANK
931 MEMORY CONTROLLER
932 FIRST IMAGE PROCESSING UNIT
932A CLAMP PROCESSING UNIT
932B WB PROCESSING UNIT
932C DIGITAL GAIN PROCESSING UNIT
932D DEMOSAIC PROCESSING UNIT
932E COLOR MATRIX PROCESSING UNIT
932F GAMMA PROCESSING UNIT
932G YC PROCESSING UNIT
932H FIRST ENLARGEMENT PROCESSING UNIT
932I IMAGE ENHANCEMENT PROCESSING UNIT
932J SECOND ENLARGEMENT PROCESSING UNIT
932K SDI CONVERTER
933 SECOND IMAGE PROCESSING UNIT
934 THIRD IMAGE PROCESSING UNIT
935 FOURTH IMAGE PROCESSING UNIT
941 LIGHT SOURCE CONTROL UNIT
942 IMAGING CONTROL UNIT
943 MODE SWITCHING UNIT
Ar1 FIRST DIVIDED AREA
Ar2 SECOND DIVIDED AREA
Ar3 THIRD DIVIDED AREA
Ar4 FOURTH DIVIDED AREA
Ar5 FIFTH DIVIDED AREA
Ar6 SIXTH DIVIDED AREA
Ar7 SEVENTH DIVIDED AREA
Ar8 EIGHTH DIVIDED AREA
Ar9 NINTH DIVIDED AREA
Ar10 10TH DIVIDED AREA
Ar11 11TH DIVIDED AREA
Ar12 12TH DIVIDED AREA
CN1, CN2 CONNECTOR
P1 FIRST STORAGE POSITION
P2 SECOND STORAGE POSITION
P3 THIRD STORAGE POSITION
P4 FOURTH STORAGE POSITION
P5 FIFTH STORAGE POSITION
P6 SIXTH STORAGE POSITION

The invention claimed is:

1. A medical image processing apparatus comprising:
a memory that temporarily stores an image;
circuitry configured to:
acquire a first captured image obtained by capturing light from an observation target that emits fluorescence when irradiated with excitation light in a second wavelength band different from a first wavelength band and is irradiated with light in the first wavelength band;
acquire a second captured image obtained by capturing the fluorescence from the observation target irradiated with the excitation light;
switch between a first observation mode and a second observation mode; and
control writing of an image into the memory and reading of an image from the memory; and
a plurality of image processing circuits that execute image processing in parallel on each input image, wherein
the circuitry,
in the first observation mode, writes the first captured image into a first memory area in the memory, reads a plurality of divided images obtained by dividing the first captured image into a number corresponding to a number of the image processing circuits from a plurality of divided areas in the first memory area, respectively, in which the plurality of divided images is written, respectively, and outputs the plurality of divided images to the plurality of image processing circuits, respectively, and
in the second observation mode, writes the first captured image and the second captured image into a second memory area and a third memory area, respectively, each having a same memory capacity as a memory capacity of each of the divided areas in the memory, reads the first captured image and the second captured image from the second memory area and the third memory area, respectively, and outputs the first captured image and the second captured image into two image processing circuits of the plurality of image processing circuits, respectively.

2. The medical image processing apparatus according to claim 1, wherein
the image processing circuits execute first image processing when the divided images or the first captured image is input and execute second image processing different from the first image processing when the second captured image is input.

3. The medical image processing apparatus according to claim 2, wherein
the first image processing includes digital gain processing for multiplying a pixel value in the divided images or the first captured image by a first digital gain to amplify the pixel value, and
the second image processing includes digital gain processing for multiplying a pixel value in the second captured image by a second digital gain different from the first digital gain to amplify the pixel value.

4. The medical image processing apparatus according to claim 2, wherein
the first image processing includes image enhancement processing for enhancing an image with first intensity for the divided images or the first captured image, and
the second image processing includes image enhancement processing for enhancing an image with second intensity different from the first intensity for the second captured image.

5. The medical image processing apparatus according to claim 4, wherein the second intensity is lower than the first intensity.

6. The medical image processing apparatus according to claim 1, wherein in the memory,
in the first observation mode, the first captured image whose total number of pixels is a first number of pixels is written into the first memory area, and
in the second observation mode, when a number of the image processing circuits is N, the first captured image and the second captured image, after thinning processing in which a total number of pixels is set to a second number of pixels equal to or less than 1/N of the first number of pixels, are written into the second memory area and the third memory area, respectively.

7. The medical image processing apparatus according to claim 1, wherein
in the second observation mode, the circuitry is configured to alternately acquire the first captured image and the second captured image in a time division manner, and
in the second observation mode, the circuitry is configured to alternately write the first captured image and the second captured image into the second memory area and the third memory area in a time division manner, and at a timing at which writing of one of the first captured image and the second captured image is started, simultaneously reads another one that has already been written, of the first captured image and the second captured image, and the one that has just been written from the second memory area and the third memory area.

8. The medical image processing apparatus according to claim 1, wherein, in the second observation mode, the circuitry is configured to write an entire first captured image and an entire second captured image into the second memory area and the third memory area.

9. The medical image processing apparatus according to claim 1, wherein, in the second observation mode, the plurality of image processing circuits thin out the first captured image.

10. The medical image processing apparatus according to claim 1, wherein, in the second observation mode, the plurality of image processing circuits thin out the second captured image.

11. The medical image processing apparatus according to claim 1, wherein, in the second observation mode, the plurality of image processing circuits thin out the first captured image and the second captured image.

12. The medical image processing apparatus according to claim 1, wherein a total number of pixels in the first captured image and in the second captured image of the second observation mode is less than or equal to the total number of pixels in the first captured image of the first observation mode.

13. A medical observation system comprising:
a light source that emits light in a first wavelength band and excitation light in a second wavelength band different from the first wavelength band;
an image sensor that generates a first captured image by capturing light from an observation target that emits fluorescence when irradiated with the excitation light and is irradiated with light in the first wavelength band, and generates a second captured image by capturing the fluorescence from the observation target irradiated with the excitation light;
a memory that temporarily stores an image;
circuitry configured to:
acquire a first captured image obtained by capturing light from an observation target that emits fluorescence when irradiated with excitation light in a second wavelength band different from a first wavelength band and is irradiated with light in the first wavelength band;
acquire a second captured image obtained by capturing the fluorescence from the observation target irradiated with the excitation light;
switch between a first observation mode and a second observation mode; and
control writing of an image into the memory and reading of an image from the memory; and
a plurality of image processing circuits that execute image processing in parallel on each input image, wherein the circuitry is configured to
in the first observation mode, writes the first captured image into a first memory area in the memory, reads a plurality of divided images obtained by dividing the first captured image into a number corresponding to a number of the image processing circuits from a plurality of divided areas in the first memory area, respectively, in which the plurality of divided images is written, respectively, and outputs the plurality of divided images to the plurality of image processing circuits, respectively, and
in the second observation mode, writes the first captured image and the second captured image into a second memory area and a third memory area, respectively, each having a same memory capacity as a memory capacity of each of the divided areas in the memory, reads the first captured image and the second captured image from the second memory area and the third memory area, respectively, and outputs the first captured image and the second captured image into two image processing circuits of the plurality of image processing circuits, respectively.

14. A medical observation system comprising:
a memory that temporarily stores an image;
circuitry configured to:

acquire a first captured image obtained by capturing light from an observation target that emits fluorescence when irradiated with excitation light in a second wavelength band different from a first wavelength band and is irradiated with light in the first wavelength band;

acquire a second captured image obtained by capturing the fluorescence from the observation target irradiated with the excitation light; and switch between a first observation mode and a second observation mode; and a plurality of image processing circuits that execute image processing in parallel on each input image, wherein in the first observation mode,
the circuitry is configured to output a plurality of divided images of the first captured image to the plurality of image processing circuits, respectively, and the plurality of image processing circuits execute image processing in parallel on the plurality of divided images, and in the second observation mode,
the circuitry is configured to output the first captured image and the second captured image into two image processing circuits of the plurality of image processing circuits, and the two image processing circuits execute image processing in parallel on the first captured image and the second captured image respectively, wherein a total number of pixels in the first captured image and in the second captured image of the second observation mode is less than or equal to a total number of pixels in the first captured image of the first observation mode.

15. The medical observation system according to claim 14, wherein the circuitry is configured to, in the first observation mode, write the first captured image into a first memory area in the memory, reads the plurality of divided images obtained by dividing the first captured image into a number corresponding to a number of the image processing circuits from a plurality of divided areas in the first memory area, respectively, in which the plurality of divided images is written, respectively, and in the second observation mode, write at least one part of the first captured image and at least one part of the second captured image into a second memory area and a third memory area, respectively, each having a same memory capacity as a memory capacity of each of the divided areas in the memory, read the first captured image and the second captured image from the second memory area and the third memory area, respectively, and output the first captured image and the second captured image into two image processing circuits of the plurality of image processing circuits, respectively.

16. The medical observation system according to claim 14, wherein, in the second observation mode, the plurality of image processing circuits thin out the first captured image.

17. The medical observation system according to claim 14, wherein, in the second observation mode, the plurality of image processing circuits thin out the second captured image.

18. The medical observation system according to claim 14, wherein, in the second observation mode, the plurality of image processing circuits thin out the first captured image and the second captured image.

* * * * *